(12) United States Patent
Nunokawa et al.

(10) Patent No.: US 6,203,982 B1
(45) Date of Patent: Mar. 20, 2001

(54) METHOD FOR SCREENING COMPOUNDS REGULATING THE EXPRESSION OF HUMAN-INDUCIBLE NITRIC OXIDE SYNTHASE

(75) Inventors: Youichi Nunokawa, Osaka; Shinzo Oikawa, Kyoto; Shoji Tanaka, Hyogo, all of (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/068,880
(22) PCT Filed: Sep. 18, 1997
(86) PCT No.: PCT/JP97/03303
§ 371 Date: Sep. 2, 1998
§ 102(e) Date: Sep. 2, 1998
(87) PCT Pub. No.: WO98/12313
PCT Pub. Date: Mar. 26, 1998

(30) Foreign Application Priority Data

Sep. 20, 1996 (JP) .................................................. 8-250697

(51) Int. Cl.[7] ............................. A61K 38/21; C07H 21/04
(52) U.S. Cl. ................................................................ 435/6
(58) Field of Search ..................... 424/91; 435/6, 435/320.1, 325; 514/1, 2; 536/23.1

(56) References Cited

U.S. PATENT DOCUMENTS 5,468,630 * 11/1995 Billiar et al. ......................... 435/189
5,594,032 * 1/1997 Gonzalez-Cadavid et al. ..... 514/645

OTHER PUBLICATIONS

Citterio, A. Gazz. Chim. Ital. Electron–transfer processes by peroxydisulfate: homolytic benzylation of quinones by alkylarenes and reactions of aromatic radical cations with aromatics. Gazz. Chim. Ital. vol. 110(4):253–258.*

* cited by examiner

Primary Examiner—John S. Brusca
Assistant Examiner—William Sandals
(74) Attorney, Agent, or Firm—Karl Bozicevic; Paula Borden; Bozicevic, Field & Francis LLP

(57) ABSTRACT

A plasmid was constructed, in which the hiNOS structural gene was replaced with the luciferase structural gene as a reporter gene, with retaining functions of the hiNOS gene 5'-promoter region and 3'-untranslated region. This plasmid was stably transfected into human cell lines. The above transformed cells selectively expressed the reporter gene in the presence of inducers. It has become possible, by examining the reporter gene expression in these transformed cells, to simply and easily screen, with high sensitivity, a compound which is expected to be useful for treating inflammations and sepsis by suppressing the hiNOS expression, or a compound which is expected to be useful for antitumor, antiviral, and vascular restenosis prevention treatments by the hiNOS induction.

28 Claims, 19 Drawing Sheets

Figure 2

```
3619                                                      AGCCAGAAGCGCTATCACGAAGATATCT
                                                                    SA101        →
3647 TCGGTGCTGTATTTCCTTACGAGGCGAAGAAGACAGGGTGGCGGTGCAGCCTGGAGATGTCAGCGCTC
                                                                    SA102
3724 TGAGGGCCTACAGGAGGGTTAAAGCTGCCGGCACAGAACTTAAGGATGAGCCAGTCTCTGCATTATCTGAGTCAC
              →
             SA103
3801 AGGGCCTGGGGAGATGGAGGAGAAAGTGATATCCCCAGCCTCAAGTCTTATTCCTCAACGTTGCTCCCCATCAAGCC
3878 CTTTACTTGACCTCCTAACAAGTAGCACCCTGATTGATGGGAGCCTCCTCTCAAACTGGGCCTCCCTGTCCC
3955 TTGGAGACAAAATCTTAAATGCCAGGCCTGGCGAGTGGGTGAAAGATGAACTGCTGCTGAGTGCACCACTTCAAG
4032 TGACCACCAGAGGCTGTCTATCCGCCACCACTGTGTATTTAACTGCCTTGTACAGTTATTTATGCCTCTGTATTTAAA
4109 AAACTAACACCCAGTCTGTTCCCCATGGCCACTTGGGTCTTCCCGTATGATTCCCTGATGGAAGATATTTACATGAA
                                    ←
                                   KI102
4186 TTGCATTTTACTTTAATCAC ↑ AAAAAAAA.........
           ←
     KI101/KI104
```

Figure 4

| | |
|---|---|
| SU802 | 5'-CTTCTCAGCCACCTTGGTGAGG-3' |
| MI103 | 5'-TTCTGTGCAGTCCCAGTGAGG-3' |
| SA101 | 5'-AGCCAGAAGCGCTATCACG-3' |
| KI101 | 5'-TGTGATTAAAGTAAAATGCAATTCATG-3' |
| SA102 | 5'-GCCTGGAGATGTCAGCGCTCTG-3' |
| KI102 | 5'-GGGGAACAGACTGGGTGTTAG-3' |
| KI103 | 5'-CATTTAGGTGACACTATAG-3' |
| SA103 | 5'-GGCGCTAGCCTACAGGAGGGGTTAAAGCT-3' |
| KI104 | 5'-GCGGCCGCGTCGACGATTAAAGTAAAATGCAATTCATGT-3' |
| KI105 | 5'-GCGCGGATCCGGCCCACTCTCCTAAG-3' |

Figure 6 wild-type hiNOS cDNA sequence     5'-ATGGCCTGTCCTTGGAAATTTCTGTT-3' mutant sequence     5'-ATGGCCTGTCCCATGGAAATTTCTGTT-3'

Figure 7

```
3724 TGAGGGCCTACAGGAGGGGTTAAAGCTGCCGGCACAGAACTTAAGGATGGAGCCAGCTCTGCATTATCTGAGGTCAC
3801 AGGGCCTGGGGAGATGGAGAAAGTGATATCCCCCAGCCTCAAGTCTTATTCCTCAACGTTGCTCCCCATCAAGCC
3878 CTTTACTTGACCTCCTAACAAGTAGCACCCTGGATTGATCGGAGCCTCTCTCAAACTGGGGCTCCCTGGTCCC
3955 TTGGAGACAAAATCTTAAATGCCAGGCCTGGCAGTGGTGTATTTAACTGCTGCTGAGTGCACCACTTCAAG
4032 TGACCACCAGGAGGTGCTATCGCACCACTGTGTATTTAACTGCCTTGTGTACAGTTATTTATGCCTCTGTATTTAAA
4109 AAACTAACACCCAGTCTGTTCCCCATGGCCACTGGGTCTTCCCTGTATGATTCCTTGATGGAGATATTTACATGAA
4186 TTGCATTTTACTTTAATCAGACTGTATGCGTGTGTGGGTGTGTTTTGTAGGGAAAGCTCTTCTCAGAGTGGGAGCTGG
     TGGGTGTCACAGCCTGACAGATCCCCGACAGGGACACCCCAGCCAGTCCATGGCTCCTCCTGAAATGGCTGCCAG
     GTGTGCCAGCAGCAGATGGAGCTTCGTGCTGGTCCAAAGACCTGTGGTAGGGCAGGGCGCAGGGGCCTGCCTCCCAC
     ACAAAGTATCTGAAACGGGGTCTGGTGGGATTGTCGCATAAGGCCAGTGTTTGCGAGGAAGGCCTTGAGCTT
     CTTCTTGGACACTGTCTTAGAAAGCGTTTTGCTCTGGGCCAGTCTCATGCGAGACTGTGTGCCTTGGCCAGTA
     CGGATGTGGTCCTGGAAGGCAGCGTGTCGAGTGTGGGCCACACATCCCTGCCTGAGGGACTGGGACCC
     TCTGGGTTTGGAGCAGGCCAAGGAGTGGGCCCGTTTCCTTCCTCCTGGTCAGAACCCAAAA

AGGAGCTCAGCGGGCGGGCCACTGGGNNNNNNNNNNNNNNNN
```

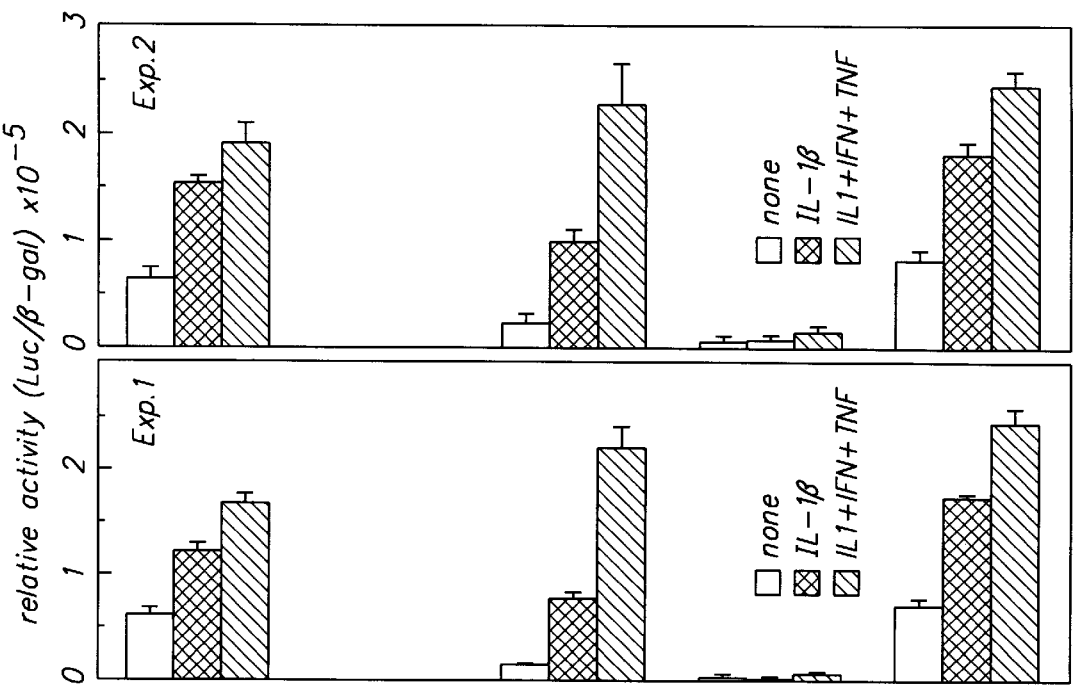
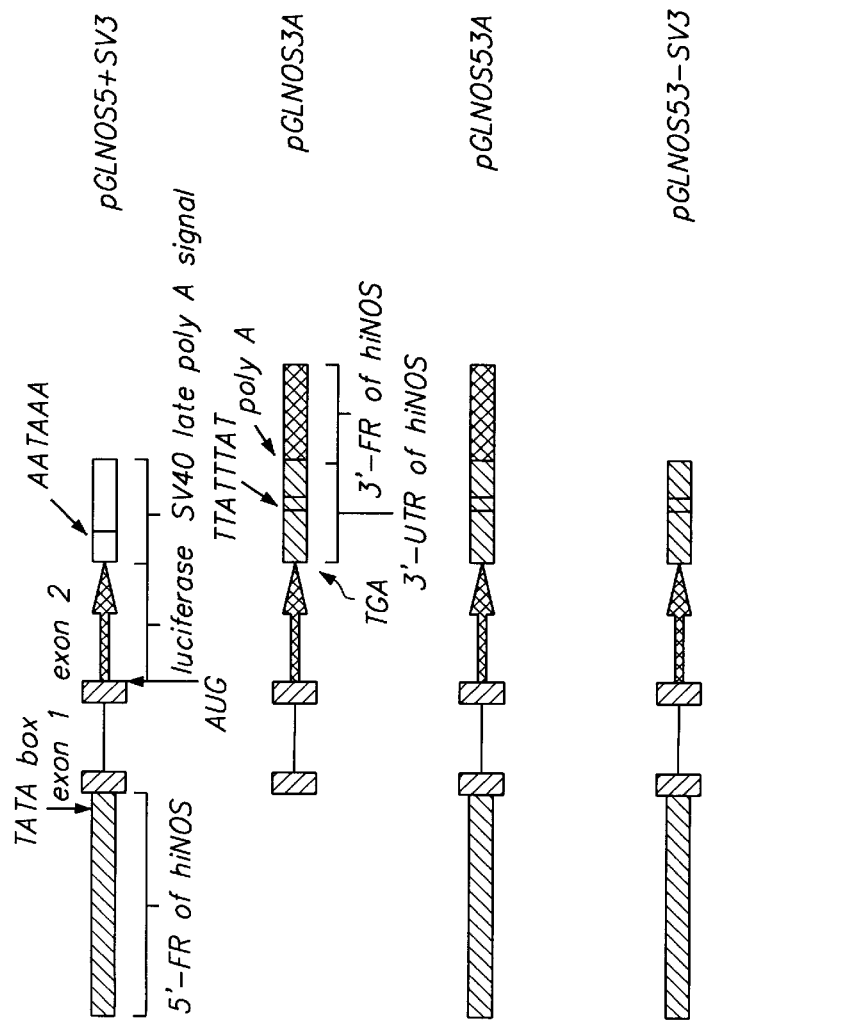
FIG. 9

METHOD FOR SCREENING COMPOUNDS REGULATING THE EXPRESSION OF HUMAN-INDUCIBLE NITRIC OXIDE SYNTHASE

TECHNICAL FIELD

The present invention relates to a method for screening a compound capable of influencing the expression level of human inducible nitric oxide synthase, more specifically to a method for screening a compound capable of controlling the expression of the enzyme.

BACKGROUND ART

Since when nitric oxide (NO) was identified as a vasodilation factor, it has been found to be a physiologically active substance that plays an important role in regulating the biological functions. In addition to the above function, it was reported that NO has a platelet aggregation suppressing effect, a neurotransmitter releasing effect, and an effect to cause macrophage to exhibit antitumor and bactericidal activities (Moncada, S. and Higgs, A. (1993) N. Engl. J. Med. 329, 2002–2012).

NO is biologically synthesized by NO synthase (NOS) from L-arginine as a substrate. At present, three isozymes of this enzyme have been confirmed to exist (the brain type, the endothelial type, and the inducible type). Their chromosomal localization is also known (Knowles, R. G. and Moncada, S. (1994) Biochem. J. 298, 249–258).

Among these, the inducible type NOS (iNOS) can be expressed by applying endotoxins or cytokines to such cells as vascular smooth muscle cells (VSMC), hepatocytes, chondrocytes, or glial cells, to thereby induce gene transcription. Recently, mice deficient in this gene (knockout mice) have been developed. It was reported that the mice possess weaker defense capability against infections but exhibits alleviated symptoms of inflammation and sepsis as compared with the wild type (Wei, X. et al., (1995) Nature 375, 408–411; MacMicking, J. D. et al., (1995) Cell 81, 641–650). There is a report showing that iNOS is induced in any species by inflammatory conditions and that the suppression of its enzymatic activities and expression are effective for alleviating the inflammatory symptoms (Moncada, S. and Higgs, E. A. (1995) FASEB J. 9, 1319–1330). Further, in a sepsis model, the administration of iNOS enzyme inhibitors were found to be effective (Kerwin, J. F. et al., (1995) J. Med. Chem. 38, 4343–4362).

The endothelial type NOS (eNOS), on the other hand, was reported to participate in the homeostasis, especially in suppressing the rise in blood pressure, and is considered to play an important role in biological functions. Consequently, it has been desired to find a compound that does not affect the eNOS activity but specifically inhibits iNOS activity. However, since the primary structural domains of the proteins that inhibit the activities of these isozymes resemble each other very closely, none of the present NOS enzyme inhibitors are satisfactory in terms of their specificities.

On another aspect, it was confirmed that substances that generate NO can suppress vascular hypertrophy, thereby preventing arteriosclerosis and post-angioplasty vascular restenosis in animal models (Garg, U. C. and Hassid, A. J. (1989) J. Clin. Invest. 83, 1774–1777, Cooke, J. P. et al., (1992) J. Clin. Invest. 90, 1168–1172). It was also reported that the forced expression of the NOS gene in VSMC results in an increase of NO production accompanied by the suppression of hypertrophy of the inner membrane of VSMC (von der Leyen, H. E. et al., (1995) Proc. Natl. Acad. Sci. USA 92, 1137–1141). Therefore, it is expected that the generation of NO at the site of vascular hypertrophy can be effective in treating or preventing vascular hypertrophy.

The above-described facts suggest that, if iNOS isozyme-specific gene expression-regulating compounds are found out, the inhibitors will be useful as anti-inflammatory agents, while the inducers will be useful as agents which lead to therapeutic improvements in especially cardiovascular field.

Reporter genes are utilized for monitoring the expression of a certain gene simply and easily with high sensitivity, (Yokota, T., and Arai, K. (1993) Biomanual Series 4, Youdosha). Reporter genes are used instead of directly detecting the test gene expression and such genes that are widely being used at present include those whose expression products can be easily assayed, such as chloramphenicol acetyl transferase (CAT), β-galactosidase (β-Gal), and luciferase. The activity of the test DNA, whose regulatory activity is to be measured, can be detected with high sensitivity by inserting it into a plasmid at either upstream or downstream of the reporter gene.

The reporter genes used to examine the regulation of the mouse iNOS (miNOS) gene expression and the results were reported. For example, within the upstream region of the miNOS transcriptional start site (hereinafter referred to as "5'-flanking region"), there was found a region at about 1.7 kb upstream from the transcriptional start site, which is involved in the induction of the miNOS gene in response to lipopolysaccharides (LPS) or IFN-γ. Furthermore, consensus sequence regions, to which transcription factors NF-κB and IRF-1 are considered to bind, were shown to be essential in the induction of the gene expression (Xie, Q. et al., (1993) J. Exp. Med. 117, 1779–1784, Vodovotz, Y. et al., (1993) J. Exp. Med. 178, 605–613, Martin, E. et al., (1994) J. Exp. Med. 180, 977–984, Xie, Q. et al., (1994) J. Biol. Chem. 269, 4705–4708). According to another report, the region was found within the 5'-flanking region of about 1.6 kb (Lowenstein, C. J. et al., (1993) Proc. Natl. Acad. Sci. USA 90, 9730–9734, Kamijo, R. et al., (1994) Science 263, 1612–1615). In both cases, however, the inducibility was less than 50-fold, which may not be strong enough to reflect the actual highly inducibility of the iNOS gene.

In contrast, it was difficult to prove the existence of cDNA of the human iNOS (hiNOS) gene. One of the reasons for this is that the cells, in which induction was effected by a single cytokine or a combination of two cytokines, were not discovered, unlike the case with the mouse macrophage or the rat VSMC. There is a report that hiNOS cannot be induced in the human macrophage even by a combination of three or more different kinds of cytokines (Weinberg, J. B. et al., (1995) Blood 86, 1184–1195). However, after the report of the first successful cloning of hiNOS cDNA by stimulating human hepatocytes with three or more different kinds of cytokines to induce the gene (Geller, D. A. et al., (1993) Proc. Natl. Acad. Sci. USA 90, 3491–3495), many reports of the hiNOS cDNA cloning emerged, but the regulatory mechanism of the induction has not been elucidated (Sherman, P. A. et al., (1993) Biochemistry 32, 11600–11605, Charles, I. G. et al., (1993) Proc. Natl. Acad. Sci. USA 90, 11419–11423, Hokari, A. et al., (1994) J. Biochem. 11, 575–581). At the same time, the complete structure of the hiNOS structural gene (FIG. 1) and its nucleotide sequence of the 5'-flanking region of approximately 0.4 kb were elucidated (Chartrain, N. A. et al., (1994) J. Biol. Chem. 269, 6765–6772).

On the other hand, the present inventors succeeded in cloning the iNOS gene from the rat vascular smooth muscle and reported to suggest that its cDNA is uniform throughout different tissues and species (Nunokawa, Y. et al., (1993) Biochem. Biophys. Res. Commun. 191, 89–94). Furthermore, the present inventors cloned a stretch of over 3.2 kb DNA, which is expected to contain the iNOS gene promoter region, determined the nucleotide sequence of the 5'-flanking region of approximately 1.5 kb, and reported that the sequence contains, as does the miNOS gene sequence, a consensus sequence thought to be regulated by interferon (IFN)-rand transcription factor NF-κB (Nunokawa, Y., et al., (1994) Biochem. Biophys. Res. Commun. 200, 802–807).

Thereafter, 16 kb of the 5'-flanking region of the hiNOS gene was studied using a reporter gene. The result showed that a region necessary for the induction of the hiNOS gene exists between 3.8 kb and 16 kb upstream from the transcriptional start site (de Vera, M. E. et al., (1996) Proc. Natl. Acad. Sci. USA 93, 1054–1059). However, the inducibility was still about 10-fold and the expression with no stimulation was quite strong. Thus, this report provides insufficient explanation for the actual and powerful induction of iNOS gene. In addition, the region up to 3.7 kb upstream from the transcriptional start site of the hiNOS gene was shown not to be involved in induction of the gene expression (Laubach, V. E. et al., (1994) Abstract Book of the 1st International Conference of Biochemistry and Molecular Biology of Nitric Oxide (UCLA Sunset Village, Los Angeles, Calif., USA), A16, Kleinert, H. et al., (1996) Mol. Pharmacol. 49, 15–21).

The present inventors generated cells transfected with a plasmid containing approximately 3.2 kb of the 5'-flanking region of the hiNOS gene, which had been previously cloned, linked to a reporter gene. The results indicated, contrary to those reported by using the miNOS promoter region, but similar to those reported by other groups using the hiNOS gene, that the reporter gene has been expressed even under non-inducing conditions when the 5'-flanking region of approximately 3.2 kb is used, and that the inducibility by cytokines is either absent or very weak (Nunokawa, Y. et al., (1996) Biochem. Biophys. Res. Commun. 223, 347–352). Moreover, the reporter gene expression was detected even in the cells transfected with the above plasmid that do not show the hiNOS induction by various cytokines (Nunokawa, Y. et al., (1996) Biochem. Biophys. Res. Commun. 223, 347–352). That is, it was found that the control of the hiNOS gene expression by inducers such as cytokines cannot be explained based solely on the promoter region which was inferred from the reported results with the miNOS gene. However, the reason for this has not been made clear at all so far.

DISCLOSURE OF THE INVENTION

The object of the present invention is to provide a method for screening a substance capable of suppressing or inducing the expression of the hiNOS gene by identifying the region (s) of the hiNOS gene necessary for the control of expression by inducing factors, constructing the expression vector containing the region(s), and utilizing the vector for the screening.

As described above, when the upstream region from the hiNOS gene transcriptional start site, i.e., the 5'-flanking region, is inserted upstream of a reporter gene, the reporter gene expression is unexpectedly observed under non-inducing conditions. Based on this finding, we presumed that there was the possibility that regions other than the 5'-flanking region might control the hiNOS gene expression, and carried out experiments.

As a result of examination of the sequence of the hiNOS gene 3'-untranslated region (UTR) (SEQ ID NO:1), the present inventors have found the "AUUUA sequence," which was reported to play a role in destabilizing the mRNA, at four different places within the 3'-UTR of the hiNOS gene (FIG. 2, underlined positions). Therefore, the present inventors considered that a certain element, which destabilizes the transcription products of the gene, might control the induction of the hiNOS gene expression.

Many of the reporter genes commonly used today are constructed by incorporating an SV40-derived region having the poly A addition in order to express the mature mRNA. The plasmids so far used to confirm the hiNOS gene expression and the "pGL3 basic plasmid" that the present inventors used in the previous reports are constructed by inserting the SV40-derived region having the poly A addition (SEQ ID NO:2) at the downstream of the reporter gene (FIG. 3). If the induction of the test gene does not entirely depend on the activation of transcription but also is caused by instability of the produced mRNA, it is thus necessary to incorporate the region involved in the instability of the produced mRNA into the expression vector containing the reporter gene.

Since it was considered that the high inducibility, which had to be inherently observed, could not be realized by introducing the reporter system containing only the 5'-flanking region including the promoter, the present inventors additionally inserted a gene fragment of approximately 1 kb containing the hiNOS gene 3'-UTR and 3'-flanking region at downstream of the reporter gene. Consequently, it has been found that these regions function cooperatively with the promoter region to bring about a strong induction. That is, by inserting these regions, it has been found that the reporter gene expression is eliminated under non-inducing conditions and is activated only when cytokines are allowed to act. These results revealed the existence of the regions necessary for the induction of hiNOS gene by cytokines, which had been unknown.

Furthermore, the present inventors constructed a plasmid mimicking the genomic structure of the hiNOS gene except that the open reading frame (ORF) of the hiNOS gene was replaced by the ORF of the reporter gene. Specifically, the hiNOS gene promoter region was inserted upstream and the gene fragment of approximately 1 kb containing the hiNOS gene 3'-UTR and 3'-flanking region was inserted downstream of the reporter gene. By utilizing the human cell line transformed with the plasmid, the present inventors developed a method to screen compounds controlling the hiNOS gene expression rapidly with high sensitivity, thereby completing the present invention.

More specifically, the present invention includes each invention described in claims of this specification.

The DNAs, which constitute the hiNOS gene 5'-flanking region, 5'-UTR, 3'-UTR, and 3'-flanking region used in the present invention, include not only those isolated from human cells but also those produced synthetically. Moreover, these DNAs with chemical modifications, or whose bases are altered by substitution, deletion, or addition, can also be used as long as their ability to control the expression is retained. The DNA constituting the hiNOS gene 3'-flanking region used in the present invention is preferably the one having the sequence described in SEQ ID NO:16 (the sequence outside the enclosure in FIG. 7).

A gene encoding any peptide or protein can be used as the reporter gene of the present invention as long as one skilled in the art can measure the activity or the amount produced of its expression product (including the quantity of the mRNA produced). For example, chloramphenicol acetyl transferase (CAT), β-galactosidase (β-Gal), and luciferase can be used by measuring their enzymatic activities. Also, the secreted growth hormone or the like can be utilized by measuring its amount produced by such means as immunological antibody reaction.

The vector in the present invention containing the hiNOS gene expression control sequence can be obtained by inserting the expression control sequence into a replicable vector. Examples of the replicable vector include pUC18 and pGEM-3Z, which are known to be replicable in E. coli.

When screening substances capable of influencing the hiNOS gene expression according to the present invention, one can use the cells transformed with the vector containing the hiNOS gene expression control sequences of the present invention, or the naturally occurring cells having the expression control sequences described in the present invention and capable of controlling the hiNOS gene expression. Mammalian cells are preferably used as such cells. Transformation can be effected according to the conventional method. The transformed cells of the present invention can be either those with the vector integrated permanently into the host chromosomes or those with the vector transiently incorporated into the host. The cells with the vector permanently integrated into the host chromosomes can be selected by transfecting the host cells with the vector to be introduced containing a selection marker gene or with the vector to be introduced together with another vector containing a selection marker, and culturing the cells in a medium that allows only those cells having incorporated the selection marker to survive.

The substances capable of influencing the hiNOS gene expression according to the present invention can be screened, for example, by applying an arbitrary amount of the test substance to the transformed cells that have been cultured for a specified period of time and measuring the amount of the reporter gene expression product after a specified period of time as the enzyme activity or the amount of protein expressed. The test substance may be natural or synthetic. It may also be a single substance or a mixture of substances. For example, it is possible to test a candidate single substance independently, or a mixture of several candidate substances. In addition, it is also possible to test combinatorial libraries. Furthermore, fractions of a mixture such as cell extract can also be tested and repeatedly fractionated to ultimately isolate the substance responsible for influencing the hiNOS gene expression.

On the other hand, according to the present invention, substances capable of altering the activity of a particular substance that influences the hiNOS gene expression can be screened, for example, by applying an arbitrary amount of the candidate substance to the transformed cells that have been cultured for a specified period of time and measuring the changes in the amount of the reporter gene expression product after a specified period of time as the changes in the enzyme activity or in the amount of protein expressed. The candidate substances to be screened are defined as described above for the substances that influence the hiNOS gene expression.

The efficacy of a substance of the present invention capable of suppressing the hiNOS expression or a compound of the present invention capable of suppressing the activity of the compound that induces the hiNOS gene expression can be measured by determining the reduction in NO excretion into the culture medium, blood, or urine, upon the addition or application of the substance under the conditions that allow the cells capable of expressing mammalian iNOS or their living tissues to produce NO. The amount of NO produced can be measured by the generally known methods represented by the Griess method (Green, L. C. et al., (1982) Anal. Biochem. 126, 131–138) described in Example 5-5).

The compounds obtained through the screening method or the screening kit of the present invention as described above are those capable of influencing the amount of the hiNOS gene expressed, for example, those capable of suppressing the hiNOS gene expression, or those capable of altering the activity of a particular compound that influences the amount of the hiNOS gene expressed, for example, those capable of suppressing the activity of a compound that induces the hiNOS gene expression. A specific example of the compound capable of suppressing the activity of a compound that induces the hiNOS gene expression is the compound represented by the following structural formula,

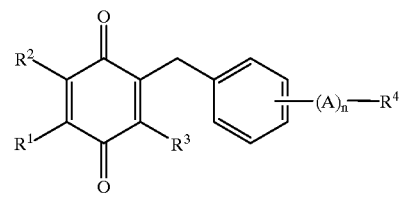

wherein $R^1$, $R^2$, and $R^3$ each independently represent a hydrogen atom, a methyl group, or a methoxy group; A represents an ethylene group or a vinylene group; n represents 0 or 1; and $R^4$ represents a hydrogen atom, a hydroxymethyl group, or a carboxyl group which may be esterified or amidated. More specifically, such compounds include the compound obtained in Example 7 of the present specification and represented by the chemical formula as shown in FIG. 17 (3-[4-(3,4-dimethoxy-6-methyl-2,5-benzoquinonylmethyl)phenyl]-1-thiomorpholino-1-oxopropane), ethyl 3-[3-(2,5-benzoquinonylmethyl)phenyl] acrylate, 3-(2,5-benzoquinonylmethyl)benzyl alcohol, 3-(2,5-benzoquinonyl-methyl)benzoic acid,3-[3-(2,5-benzoquinonylmethyl)phenyl]propionic acid, 3-[3-(2,5-benzoquinonylmethyl)phenyl]propyl alcohol, 3-[3-(2,5-benzoquinonylmethyl)phenyl]acrylic acid, 3-[4-(3,4-dimethoxy-6-methyl-2,5-benzoquinonylmethyl)phenyl] propionic acid, 2,3-dimethoxy-5-benzyl-6-methyl-1,4-benzoquinone, 3-[4-(3,4-dimethoxy-6-methyl-2,5-benzoquinonylmethyl)phenyl]propanol, and ethyl 3-[3-(3,4-dimethoxy-6-methyl-2,5-benzoquinonylmethyl)phenyl] propionate.

Since the compounds of the present invention can either directly or indirectly suppress the hiNOS gene expression, they are useful as pharmaceutical compositions for treating the pathological conditions or diseases associated with the hiNOS expression abnormality, preferably the pathological conditions or diseases accompanying an excessive expression of the hiNOS gene. For example, the compounds are useful as drugs for treating cardiac and cerebrovascular disorders, ischemic heart disease, septic shock, acute pain, rheumatism, arthritis, asthma, immunodeficiency, viral or non-viral infections, autoimmune diseases, dementia, and cancer (cattell, V. and Jensen, A., Histochem. J. Vol.27, p777–784, 1995; Ogden, J. E. and Moore, P. K., TIBTECH Vol.13, p70–78, 1995).

When the compounds of the present invention are used as pharmaceutical compositions, they can be administered either orally in the dosage form such as tablets, capsules, elixirs, microcapsules, or parenterally as injections in the form of solutions in water or in other pharmaceutically acceptable liquids, or suspensions. For example, the compounds can be formulated into the above dosage forms by mixing them with physiologically acceptable carriers, flavors, excipients, stabilizers, etc., in a generally accepted form. Additives that can be mixed in tablets include binders such as gelatin, swelling agents such as cornstarch, excipients such as crystalline cellulose, and lubricants such as magnesium stearate. In the case of capsules, liquid carriers can be contained in addition to the components described above. Sterile compositions for injection can also be formulated in the conventional manner.

An aqueous solution for injection is exemplified by an isotonic solution containing glucose, which may also be combined with appropriate solubilizers such as polyethyleneglycol. It may further contain buffers, stabilizers, preservatives, antioxidants, and soothing agents. The pharmaceutical preparations thus produced can be administered, for example, to humans and other mammals. Though the dose may vary depending on the symptoms and the like, the preparation is generally administered to an adult about 0.01 mg to about 100 mg, preferably about 0.1 mg to about 50 mg, more preferably about 1.0 mg to about 25 mg per day in the case of oral administration. In the case of parenteral administration, for example, in the form of injection, an adult is generally intravenously given about 0.001 mg to about 50 mg, preferably about 0.01 mg to about 25 mg, more preferably about 0.1 mg to about 10 mg per day.

BRIEF DESCRIPTION OF THE DRAWINGS

FIG. 2 shows (SEQ ID NO:1) the nucleotide sequence of the 3'-untranslated region (UTR) within the exon 26 of the hiNOS gene. The numerals on the left side represent the nucleotide numbers regarding the first base of the translational start site as 1. The ATTTA sequence is underlined, while the expected poly A addition site is indicated by "↑". The bold-face letters indicate the stop codon in the hiNOS gene. The nucleotide sequences on which the primers were based are marked with their designations and arrows.

FIG. 4 shows the nucleotide sequences of the primers used for the construction of the plasmids which primers are designated as follows: SU802, SEQ ID NO:3; MI103, SEQ ID NO:4; SA101, SEQ ID NO:5; KI101, SEQ ID NO:6; SA102, SEQ ID NO:7; KI102, SEQ ID NO:8; KI103, SEQ ID NO:9; SA103, SEQ ID NO:10; KI104, SEQ ID NO:11; KI105, SEQ ID NO:12.

FIG. 6 shows the nucleotide sequence substitution to create an NcoI site into the DNA of the hiNOS gene 5'-flanking region (SEQ ID NO:13). The bold-faced base "T" (wild-type hiNOS cDNA sequence; SEQ ID NO:17) was substituted with "CA" to construct the mutant plasmid.

FIG. 7 shows (SEQ ID NO:14) the nucleotide sequences of the 3'-untranslated region (UTR) and the 3'-flanking region of the hiNOS gene. The numerals on the left side represent the nucleotide numbers regarding the first base of the translational start site as 1. The encircled portion is the 3'-UTR of exon 26. The consensus sequence for the poly A addition (YGTGTTYY) within the 3'-flanking region is underlined. The boldface letters indicate the stop codon in the hiNOS gene. The nucleotide sequences on which the primers were based are marked with their designations and arrows. The sequence outside the enclosure is designated SEQ ID NO:16.

FIG. 9 shows the response of the A549 cells transiently transfected with the expression vectors against the cytokine stimulation.

BEST MODE FOR CARRYING OUT THE INVENTION

The following Example illustrates the present invention in more detail, but are not to be construed to limit the scope of the present invention.

[EXAMPLE 1]

Construction of expression vectors
1) Cloning of the hiNOS 5'-flanking Region

A probe to be used in screening of clones containing the hiNOS 5'-flanking region DNA was prepared by plaque hybridization from a human genome library consisting of 2.5×10$^6$ phages (Clontech, USA; a phage library incorporated in the EMBL3 vector).

The probe used was the cDNA amplified by polymerase chain reaction (PCR) using as the template: the rat-derived iNOS cDNA (VSM-NOS), which had been previously isolated by the present inventors (Nunokawa, Y. et al., (1993) Biochem. Biophys. Res. Commun. 191, 89–94) and using the SU802 primer (corresponding to bases –138 to –117 of the rat VSM-NOS cDNA/SEQ ID NO:3, FIG. 4) and the MI103 primer (corresponding to bases 168 to 188 of the rat VSM-NOS cDNA/SEQ ID NO:4, FIG. 4). PCR was performed using the Taq DNA polymerase (Takara Shuzo) and a buffer accompanied with it. This cDNA obviously possesses high homology to the nucleotide sequence of the 5' end of the hiNOS structural gene. The plaque hybridization was carried out using the ECL direct DNA labeling detection system (Amersham, U. K.) in accordance with the attached experimental protocol.

Figure 5:
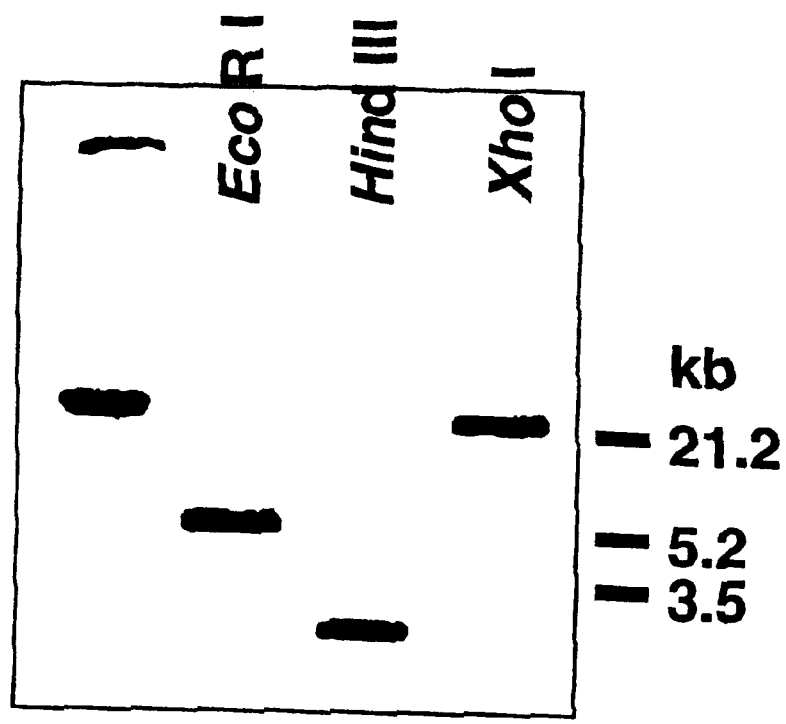
FIG. 5 is the photograph of a Southern blot of the restriction enzyme digestion fragments (digested with EcoRI, HindIII, and XhoI) of the purified phage genome containing the hiNOS gene 5'-flanking region.

Positive plaques were purified using the Qiagen Lambda kit (Qiagen, Germany) and digested with EcoRI. Southern blot analysis revealed the DNA fragment of about 5 kb hybridized with the above probe (FIG. 5).

The EcoRI-digested fragment of about 5 kb was subcloned into the EcoRI site in the pUC118 plasmid (Takara Shuzo) and a mutant plasmid, in which a base was substituted as shown in FIG. 6 (SEQ ID NO:13), was prepared in order to create an NcoI site. This procedure was carried out using Clontech's Site-Directed Mutagenesis kit in accordance with the attached experimental protocol. The mutant plasmid thus prepared was digested with KpnI and NcoI, and the resulting DNA fragment was used in the experiment of 3) below.

Figure 1:
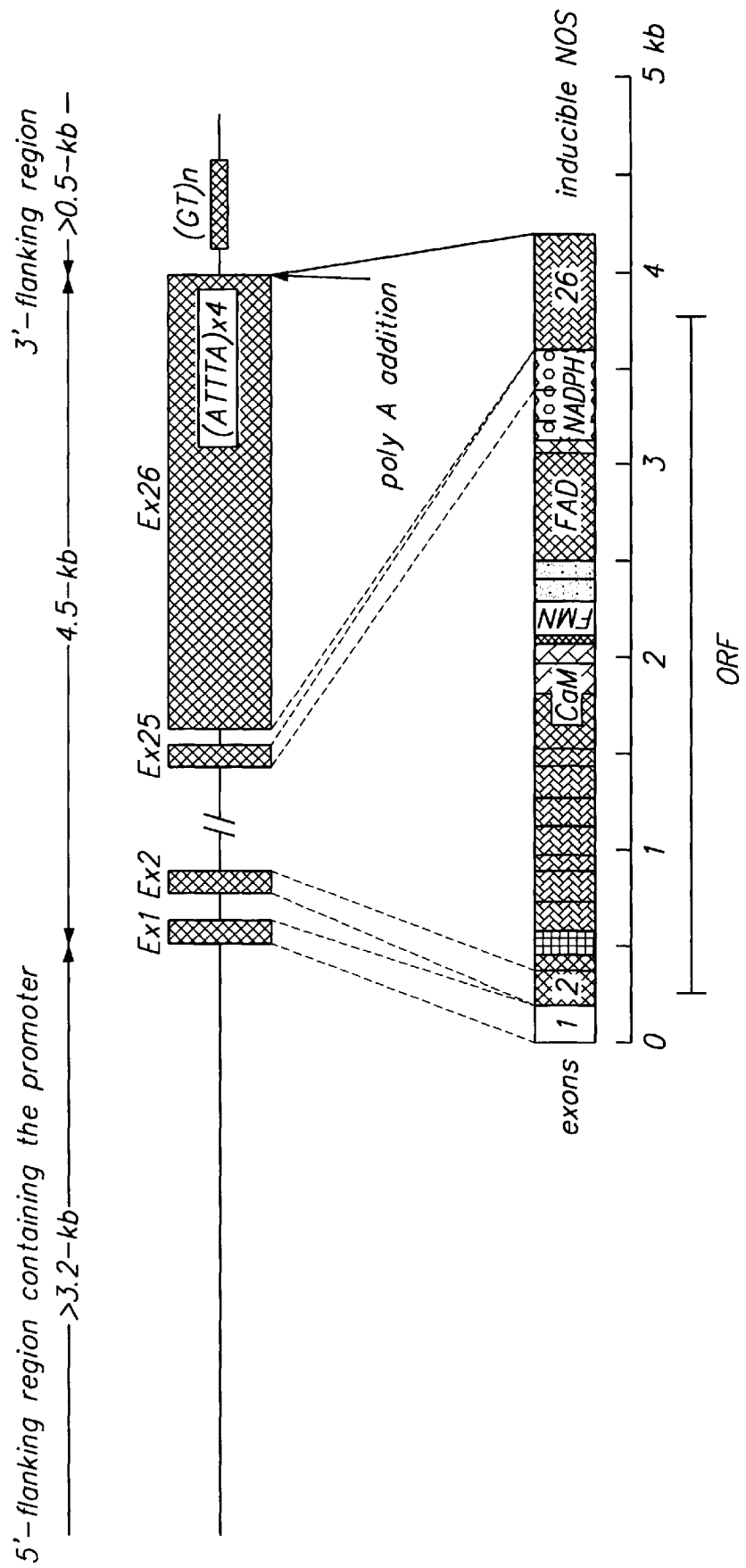
FIG. 1 shows the entire structure of the hiNOS structural gene.
Figure 3:
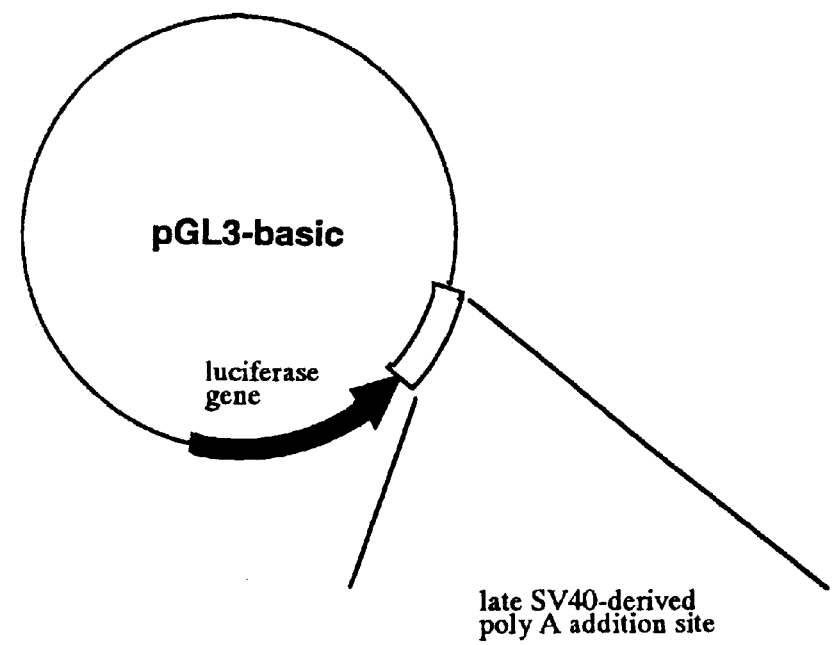
FIG. 3 shows the structure of the pGL3 basic plasmid and the nucleotide sequence of the SV40-derived poly A addition region (SEQ ID NO:2). The "Poly A signal" and the "G/T cluster" associated with the poly A addition are underlined.

2) Cloning of the hiNOS 3'-UTR and a Gene Fragment about 1 kb Downstream therefrom Containing the Region The human genome library used in 1) was divided into 60 sub-pools (about 40,000 clones per pool), and the pool containing the 3'-UTR was identified by PCR using the two kinds each of forward primers (SA101/SEQ ID NO:5, SA102/SEQ ID NO:7) and reverse primers (KI101/ SEQ ID NO:6, KI102/SEQ ID NO:8), which were designed based on the hiNOS cDNA 3'-UTR sequence (the 3' side of exon 26 in FIG. 1 and inside the encircled portion of FIG. 7). The positive pool was further subdivided into 30 sub-pools and the pool containing positive clones was identified by the PCR in the same manner as above. At this point, it was estimated that a pool contained not less than 1,000 clones. The phage population containing all the clones in the identified positive sub-pool was cultivated and phage DNA was purified using the Qiagen Lambda kit. From the result that the DNA was amplified the PCR with SA101 and KI101, the clones were confirmed to contain the hiNOS 3'-UTR. The confirmation of the results of PCR was done in the same manner as in 1).

Then, the downstream region containing the 3'-UTR was amplified by PCR using the purified DNA as a template and a forward primer (SA101) and a reverse primer (KI103/SEQ ID NO:9, FIG. 4) which was designed based on the sequence of the SP6 promoter portion of the EMBL3 right arm of the phage vector. The sequence of the amplified DNA was determined with the DYE DEOXY™ terminator DNA sequencing kit (Applied Biosystems, USA), through the direct sequencing method using the Applied Biosystems A373 DNA sequencer. The results are shown as SEQ ID NO:14 and FIG. 7.

It was confirmed that the amplified DNA is a region containing the hiNOS 3'-UTR. Based on this information, the poly A addition site based on this information was determined and a reverse primer containing an end of the 3'-UTR (KI104/SEQ ID NO:11, FIG. 4) was prepared. The KI105 reverse primer (SEQ ID NO:12, FIGS. 4 and 7) was also prepared based on the sequence of the 3'-flanking region. Using the purified DNA as a template, and SA103 (SEQ ID NO:10) and KI104, the 3'-UTR DNA of approximately 0.5 kb was amplified by PCR. Since SA103 contains an NheI recognition site on its 5' end, and KI104 contains a SalI recognition site on its 5' end, the above DNA was digested with SalI and NheI and the resulting DNA fragment (3'-UTR) was used in the experiments in 3) below.

Using the purified DNA as a template, and SA103 and KI105, the DNA of approximately 1 kb containing the 3'-UTR and the 3'-flanking region was amplified by PCR. Since SA103 contains an NheI recognition site on its 5' end and KI105 contains a BamHI recognition site on its 5' end, the above DNA fragment was digested with BamHI and NheI and the resulting fragment (containing the 3'-UTR and the 3'-flanking region) was used in the experiments in 3) below.

Figures 8A, 8C:
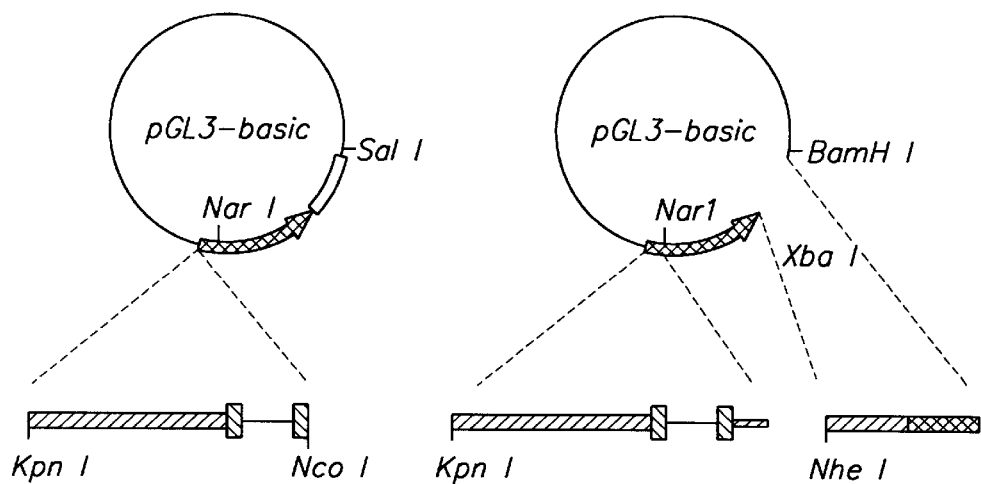
FIG. 8 shows the structures of expression vectors containing the non-structural regions of the hiNOS gene.

3) Construction of Expression Vectors Containing the Non-structural Regions of the hiNOS Gene (3-A) Construction of the plasmid (pGLNOS5+SV3) having the 5'-flanking region and the 5'-UTR inserted upstream of the luciferase gene of the pGL3 basic plasmid The pGL3 basic plasmid (Promega, USA) was digested with restriction enzymes KpnI and NcoI and the DNA fragment prepared in 1) above was inserted therein (FIG. 8A).

Figures 8B, 8D:
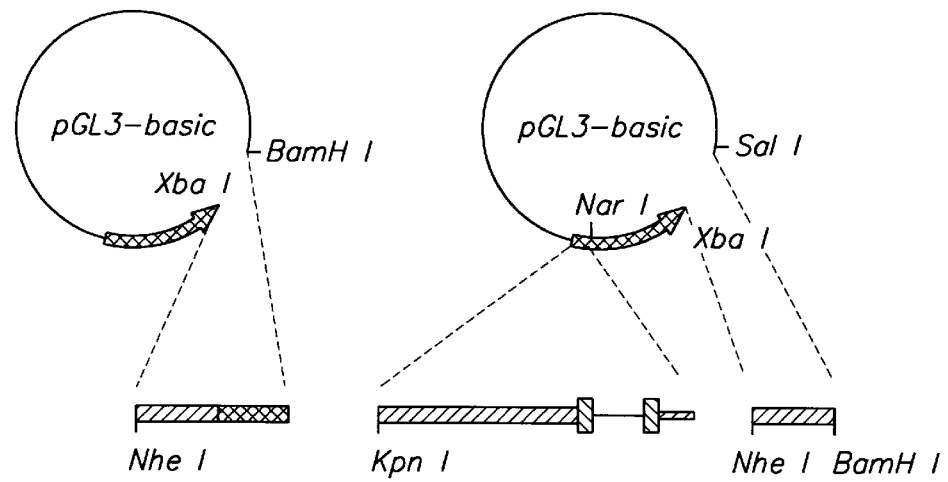

(3-B) Construction of the plasmid (pGLNOS3A) in which the region stretching from immediately downstream of the luciferase stop codon up to the SV40-derived poly A addition signal region of the pGL3 basic plasmid was deleted and an approximately 1 kb fragment containing the 3'-UTR and the 3'-flanking region of the hiNOS gene was inserted therefor immediately downstream of the luciferase gene in the pGL3 basic plasmid The pGL3 basic plasmid was digested with BamHI and XbaI and the DNA fragment prepared in 2) above (3'-flanking region) was inserted therein (FIG. 8B).

(3-C) Construction of the plasmid (pGLNOS53A) in which the hiNOS gene 5'-flanking region and 5'-UTR were inserted upstream of the luciferase gene in the pGL3 basic plasmid, the region stretching from immediately downstream of the luciferase stop codon up to the SV40-derived poly A addition signal region of the pGL3 basic plasmid was deleted, and an approximately 1 kb fragment containing the 3'-UTR and the 3'-flanking region of the hiNOS gene was inserted therefor The pGL3 basic plasmid was digested with BamHI and XbaI and the DNA fragment prepared in 2) above (containing the 3'-UTR and the 3'-flanking region) was inserted therein. The resulting plasmid was digested with restriction enzymes KpnI and NarI and the DNA fragment prepared in 1) above was inserted therein (FIG. 8C).

(3-D) Construction of the plasmid (pGLNOS53-SV3) in which the region stretching from immediately downstream of the luciferase stop codon up to the SV40-derived poly A addition signal region of the pGLNOS5+SV3 plasmid prepared in (3-A) above was deleted, and the 3'-UTR of the hiNOS gene was inserted therefor immediately downstream of the luciferase gene The pGL3 basic plasmid was digested with restriction enzymes XbaI and SalI, the DNA fragment (3'-UTR) was inserted therein, and it was digested with KpnI and NarI. The DNA fragment obtained by the digestion of pGLNOS5+SV3 with KpnI and NarI was then inserted into this plasmid (FIG. 8D).

Figure 8E:
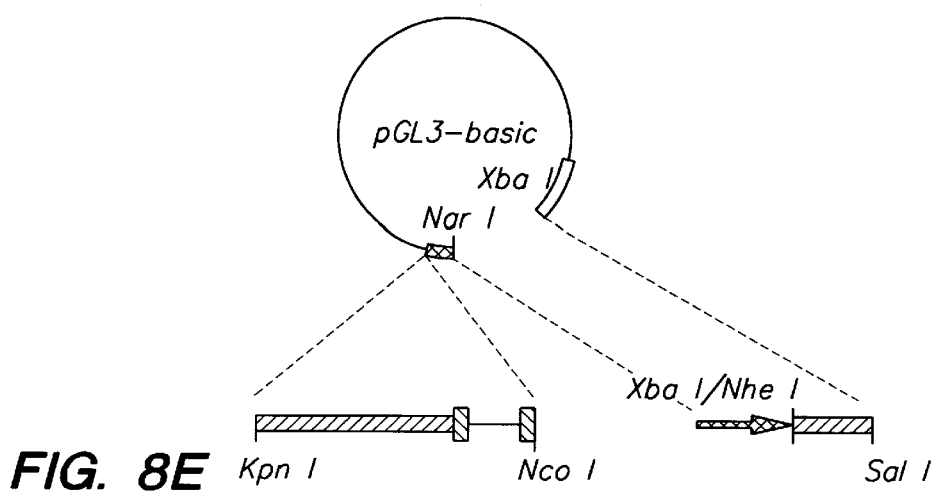

(3-E) Construction of the plasmid (pGLNOS53+SV3) in which the 3'-UTR of the hiNOS gene was inserted immediately downstream of the luciferase gene in the pGLNOS5+SV3 plasmid prepared in (3-A) above The pGLNOS53-SV3 plasmid prepared in (3-D) above was digested with restriction enzyme SalI, the ends were made blunt by the DNA Blunting Kit (Takara Shuzo), and it was digested with NarI. The DNA fragment produced by digesting the pGLNOS5+SV3 plasmid with XbaI, the ends were made blunt using the DNA Blunting Kit, followed by digestion with NarI. The resulting DNA fragment was inserted into the above plasmid (FIG. 8E).

[EXAMPLE 2]

Reaction of the A549 cells transiently transfected with the expression vectors against the cytokine stimulation A human lung cancer-derived cell line, A549, which is known to express hiNOS in response to the cytokine stimulation, was obtained from ATCC (Catalog #CCL185) and cultured in the GIT medium (Wako Pure Chemical Industries, Ltd.) in an atmosphere of 5% $CO_2$ incubator. The expression vectors shown in FIG. 8 were each transfected transiently into the A549 cells using LIPOFECTAMINE (Life Technologies Inc., USA). Six hours after adding either human IL-1β (1 ng/ml) or human IL-1β (1 ng/ml)+human IFN-γ (1,000 U/ml)+human TNF-α (500 ng/ml) (this mixture will be sometimes hereinafter referred to as "CM"), the response was examined (FIG. 9). The luciferase activity was measured in accordance with the protocol for the Luciferase Assay System (Promega). The ARGUS-50 luminometer (Hamamatsu Photonics) was used for detection. Human IL-1β was purchased from Genzyme (USA). Human IFN-γ and the human TNF-α were produced at Suntory Institute for Biomedical Research by the conventional method. In order to normalize the assay in this experiment, a β-gal expression vector (pSv-β-gal, Promega) was co-transfected as a control vector and the results were extrapolated.

When pGLNOS5+SV3 was introduced, a high level expression was observed without the stimulation and the strong induction by cytokines was not observed. When pGLNOS53+SV3 was introduced, the result was the same as in the case that pGLNOS5+SV3 was introduced. In addition, when pGLNOS53-SV3 was introduced, no increase of the reporter expression was observed in both cases of no stimulation and stimulation with the cytokine. On the other hand, when pGLNOS53A (the plasmid containing the 3'-UTR and the 3'-flanking region of the hiNOS gene) was used, almost no luciferase expression occurred without the stimulation, whereas high expression was observed upon the addition of IL-1β and the expression level became much higher by the addition of the three kinds of cytokines. Namely, it was found that the regulation of the hiNOS gene expression requires the presence of both the 3'-UTR and the 3'-flanking region.

[EXAMPLE 3]

Gene sequence possibly involved in the hiNOS inducibility

By means of the gel shift method, it is possible to observe the binding of proteins by cytokine stimulation to the double-stranded DNA (5'-AACTGTACACAAGCTGGGGACACTCCCTTTGGAAA-3'/SEQ ID NO:15) which corresponds to the nucleotides −131 to −97 upstream of the transcriptional start site of the hiNOS gene. The above DNA sequence contains the consensus sequence to which NF-κB is expected to bind. The gel shift method was performed by modifying the above double-stranded DNA with digoxigenin (DIG) (using the Gel Shift Assay kit, Boehringer Mannheim, Germany), incubating it with the nuclear extracts from A549, and subjecting it to 7.5% polyacrylamide gel electrophoresis (Bio-Rad, USA)

at 4° C. The cellular nuclear extracts were obtained from the cells stimulated with IL-1β (1 ng/ml) or with CM for 4 hours or from the non-stimulated cells using the method of Schreiber et al. (Schreiber, E. et al., (1989) Nucleic Acids Res. 17, 6419). The DNA obtained from the gel following the gel electrophoresis was transferred onto the ZETA-PROBE™ nylon membrane (Bio-Rad) by electroblotting (using the apparatus made by Atto), and the DIG-labeled DNA was detected with a chemiluminescent DIG-recognition antibody.

Figure 10:
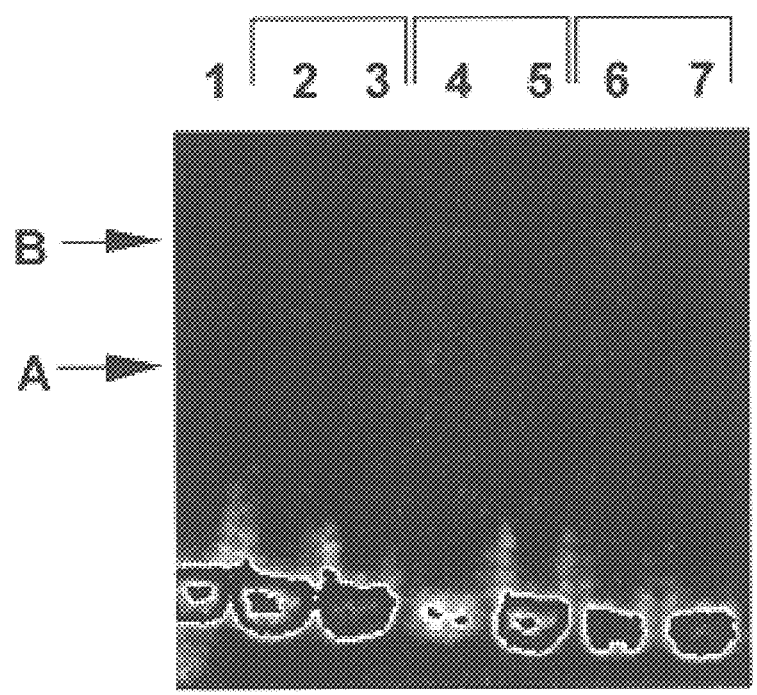
FIG. 10 is the photograph of a gel shift assay using the nuclear extracts from the A549 cells stimulated with cytokines.

FIG. 10 show the results. It was found that a protein (A), which exists in the A549 nuclear extract in the absence of stimulation, binds to the above sequence (corresponding to band A of FIG. 10) and that another binding protein (B), which exists in the A549 nuclear extract is induced to bind to the sequence by the stimulation with IL-1β or CM (corresponding to band B of FIG. 10). These results revealed that 5'-flanking region of the hiNOS gene contains, as does miNOS, the region to which NF-κB binds upon cytokine stimulation.

[EXAMPLE 4]

Construction of A549 cells stably transfected with expression vectors (A549/hiNOSLuc) and their response to cytokine stimulation pGLNOS53A and pSV2neo (Clontech) were co-transfected into A549 cells using LIPOFECTAMINE™ (Life Technologies Inc., USA) and the cells stably transfected with pGLNOS53A (A549/hiNOSLuc) were selected by adding G418 sulfate (1 mg/ml, Life Technologies Inc.) to the medium.

Six clones were arbitrarily chosen from plural G418 resistant cells. IL-1β (1 ng/ml) or CM was added thereto and the response was compared after 24 hours with the non-stimulated clones. As a result, all 6 clones expressed luciferase only when they were stimulated with cytokines. These data indicated that the structure of the plasmid to be introduced is important for the induction of the gene expression, but it is not influenced by the position on the chromosome of the introduced gene.

[EXAMPLE 5]

Comparison of the response of A549/hiNOSLuc to cytokine stimulation and the hiNOS expression pattern A clone (A5) was chosen from among the G418 resistant cells obtained in Example 4 to examine the induction of luciferase expression by a variety of substances listed below. (No particular reason exists for the choice of A5.) The A5 cells were spread onto the 96-well plate to about 10,000 cells/100 μl per well and cultured for 24 hours. The following substances were added to each well and, after 6 or 24 hours, the luciferase activity was measured in accordance with the Luciferase Assay System (Promega) protocol. The ARGUS-50 luminometer (Hamamatsu Photonics) was used for detection.
1) IL-1β

The luciferase expression was observed within at least 6 hours by IL-1β (1 ng/ml) stimulation. However, the same amount of IL-1β alone did not change the expression level even after 24 hours of stimulation as well as after 6 hours (FIG. 11).
2) IFN-γ

Figure 11:
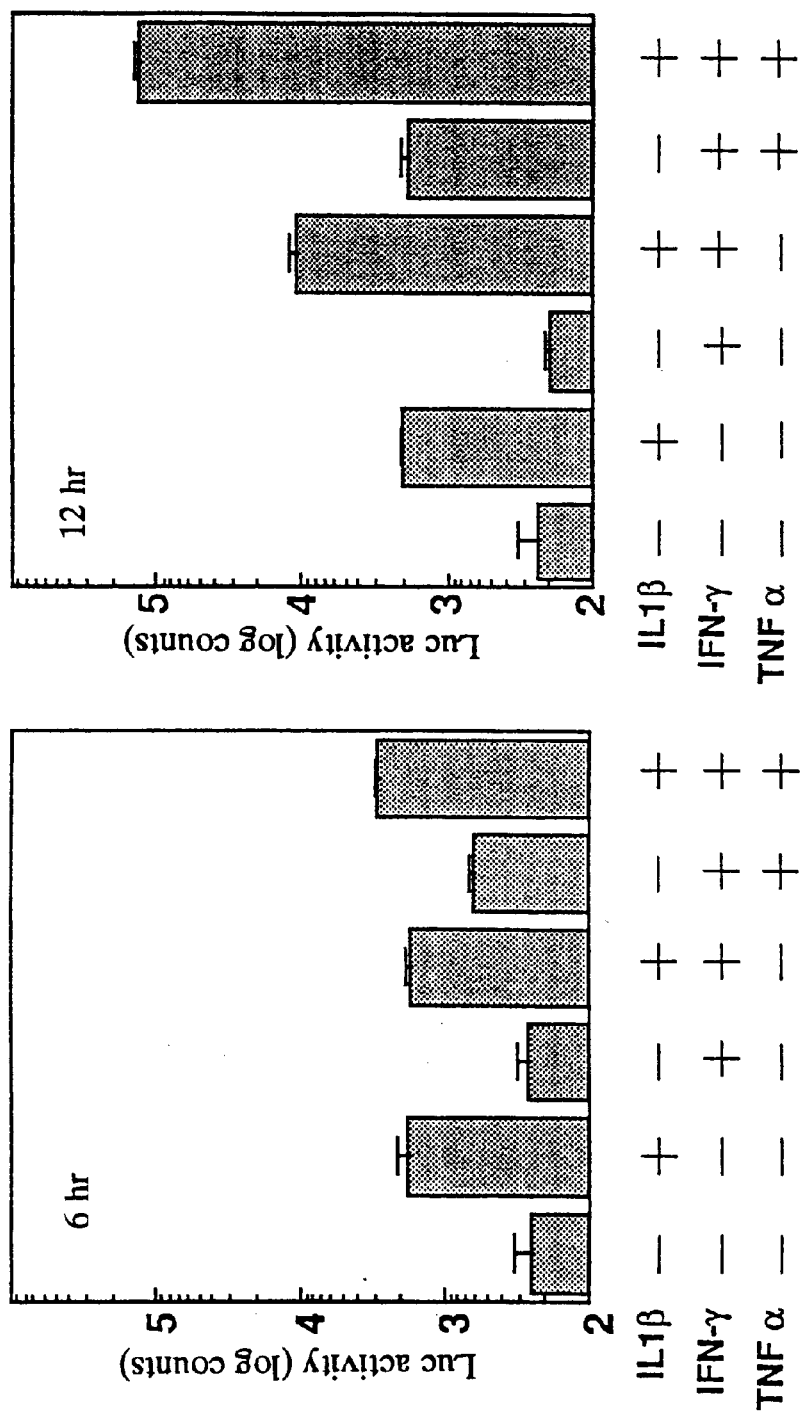
FIG. 11 shows the response of the A 549 cells stably transfected with the expression vector (hiNOSLuc) against the cytokine stimulation.

IFN-γ (1,000 U/ml) stimulation did not cause an increase of the expression (FIG. 11).

3) TNF-α

TNF-α (500 ng/ml) stimulation did not cause an increase of the expression (FIG. 11).

4) Combination of Cytokines

When the 3 kinds of cytokines used in 1) through 3) were added together (CM), a weak increase of the expression was observed within 6 hours, while a very strong expression was observed after 24 hours (FIG. 11). The level of the expression is estimated to be about 500 times as high as the background (100 to 200 counts), which agrees with the report that hiNOS is strongly induced by CM. Additionally, IL-1β (1 ng/ml)+IFN-γ (1,000 U/ml) also induced the expression strongly, and the 24-hour culture in the presence of the two cytokines resulted in a stronger increase of the expression than IL-1β (1 ng/ml) alone (FIG. 11). Also even in the absence of IL-1β, the stimulation by IFN-γ and TNF-acaused induction after 24 hours.

5) Comparison with the Results Obtained using the Griess Method

Figure 12:
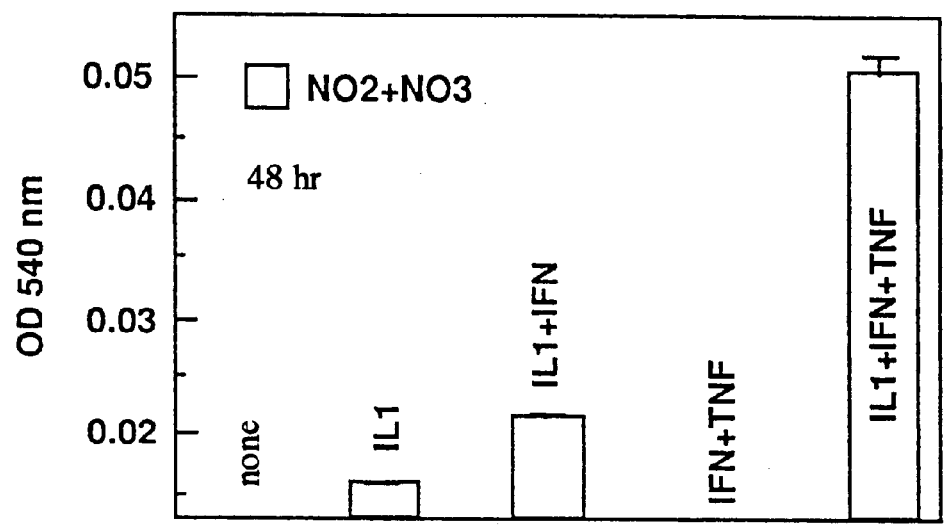
FIG. 12 shows the response of the A 549 cells against the cytokine stimulation, measured by Griess method.

The Griess method, which utilizes the diazotization reaction, is known as a method of indirectly monitoring the production of NO by the cell (Green, L. C. et al., (1982) Anal. Biochem. 126, 131–138). In the method, Griess reagent, which is a mixture of naphthylethylenediamine (Kanto Chemical, Tokyo) and sulfanilic acid (Nacalai Tesque), is reacted with the $NO_2^-$ ion in the culture medium to determine color development by the multititer plate reader (Molecular Devices) by measuring absorbance at 540 nm. When the accumulated NO in the A549 cell culture 48 hours after the cytokine stimulation was measured by this method, the production of NO stimulated by IL-1β (1 ng/ml) or CM was observed (FIG. 12).

These results conform to the assay results of 1) through 4) where the luciferase expression was measured. Therefore, it was confirmed that the hiNOS-derived NO production can be readily calculated by detecting the luciferase expression. (The sensitivity of the method based on the luciferase expression was more than 100 times as high as that of the Griess method.)

[EXAMPLE 6]

Figure 13:
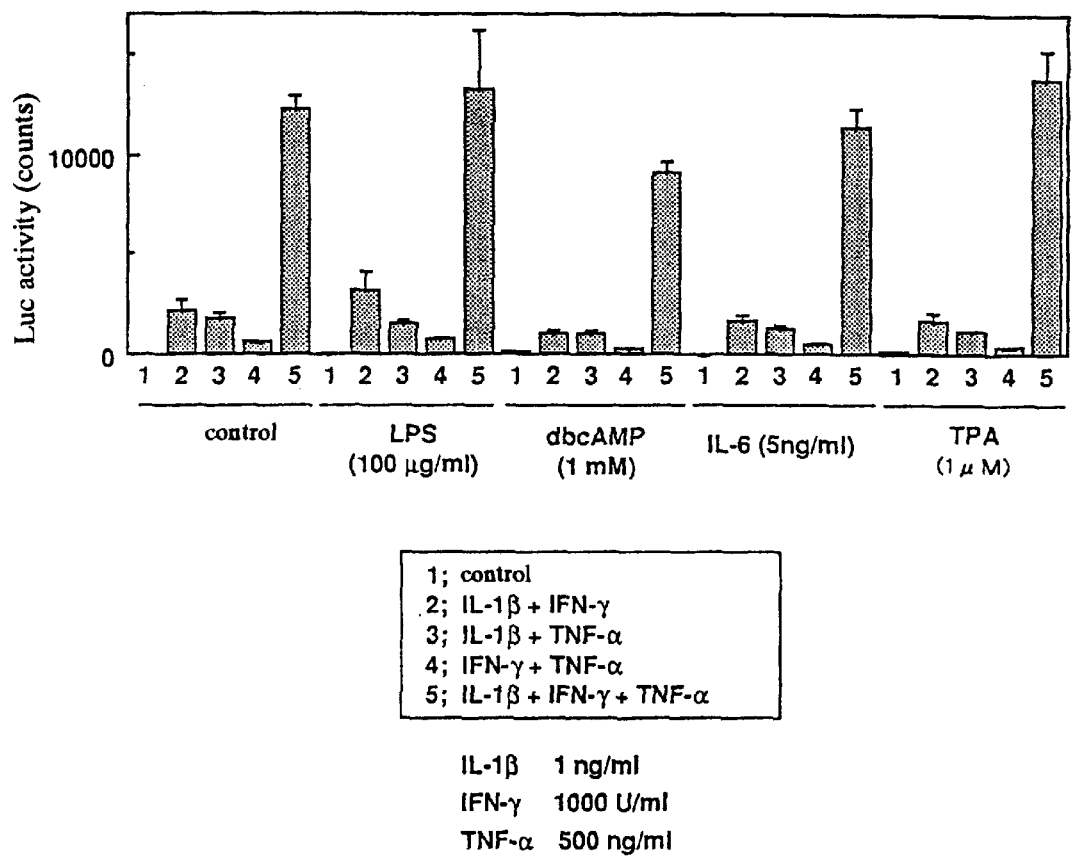
FIG. 13 shows the effects of LPS, IL-6, cAMP, and TPA on the response of the A 549 cells stably transfected with the expression vector (hiNOSLuc) against the cytokine stimulation.
Figure 14:
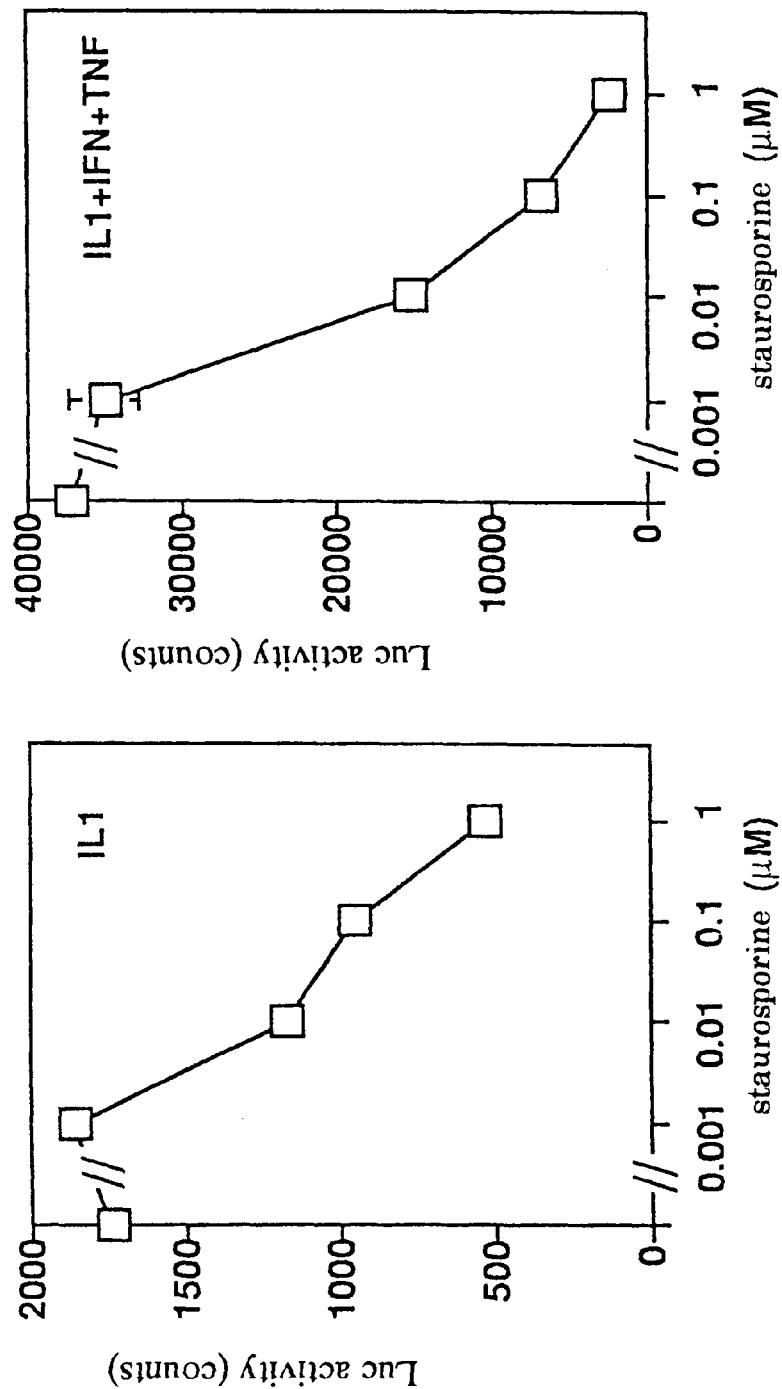
FIG. 14 shows the effects of the protein kinase inhibitor, staurosporine, on the induced gene expression by cytokines.

Effects of compounds expected to influence the iNOS expression on the assay system of the present invention 1) Effects of LPS (lipopolysaccharides), IL-6, cAMP, TPA (tetradecanoylphorbol acetate), and protein kinase inhibitors LPS (Sigma, USA), IL-6 (Genzyme), CAMP (dibutyryl form, Sigma), and TPA (Nacalai Tesque) were reported to induce iNOS in experimental systems using mouse or rat cells. The luciferase expression was measured in the same manner as in Example 5 in the presence of these compounds. As a result, these substances hardly influenced not only the control levels but also the activation by cytokines (FIG. 13). These results revealed that these substances hardly influence the assay system described in Example 5. On the other hand, the protein kinase inhibitor, staurosporine (Wako Pure Chemical Industries), was found to suppress the induced gene expression by IL-1β (1 ng/ml) or CM at a concentration of not more than 1 μM (FIG. 14).

2) Effects of Glucocorticoid

Figure 15:
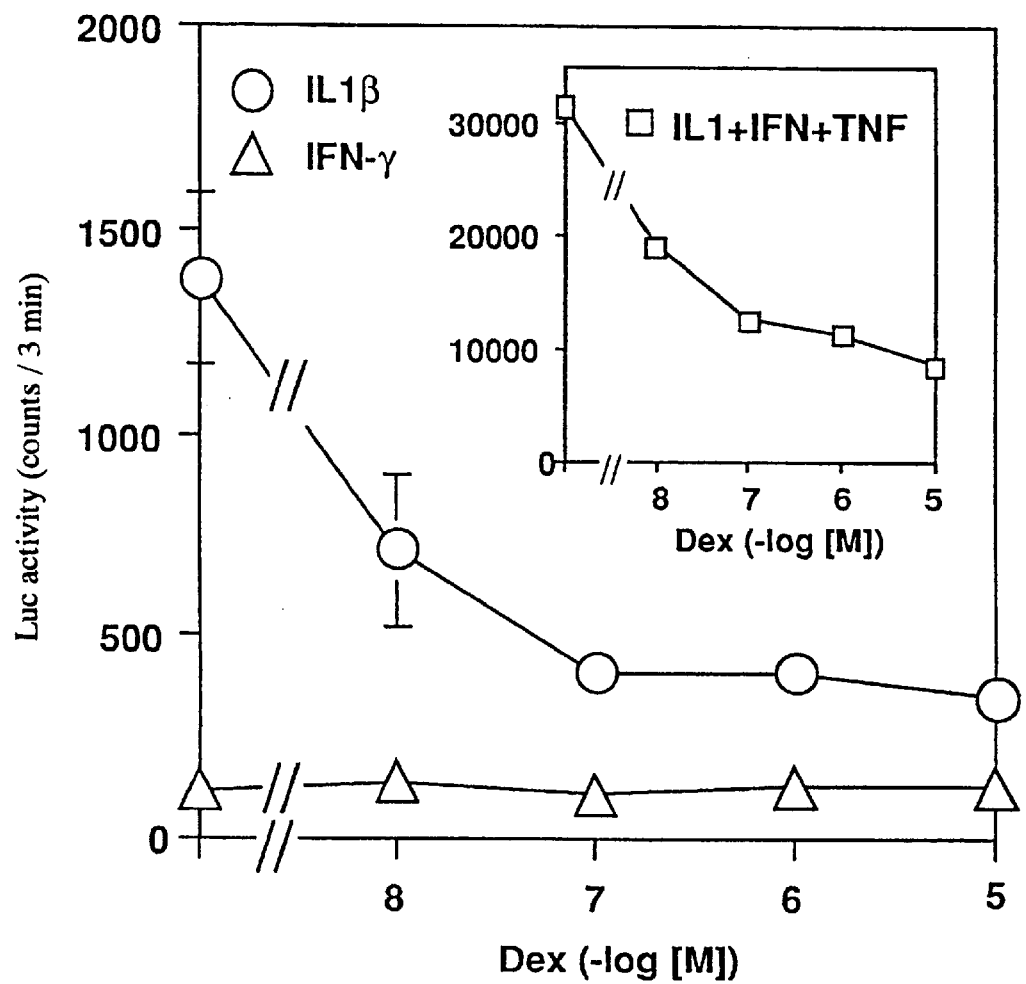
FIG. 15 shows the effects of dexamethasone on the induced gene expression by cytokines.

Dexamethasone (Dex) (Wako Pure Chemical Industries) possesses a powerful antiinflammatory effect. One of its mechanisms is known to be attributed to the suppression of activation of the transcription factor NF-κB (Ray, A. and Prefontaine, K. E. (1994) Proc. Natl. Acad. Sci. USA 91, 752–756). It was also reported to suppress the iNOS expression (Radomski, M. W. et al., (1990) Proc. Natl. Acad. Sci. USA 87, 10043–10047). The luciferase expression was measured in the same manner as in Example 5 in the presence of dexamethasone, and found that the induced gene expression by IL-1β (1 ng/ml) or CM was suppressed at a concentration of not more than 10 μM (FIG. 15). Moreover, the suppressive effect disappeared if it was added after 1 hour of cytokine stimulation.

3) Effects of Protease Inhibitors

Figure 16:
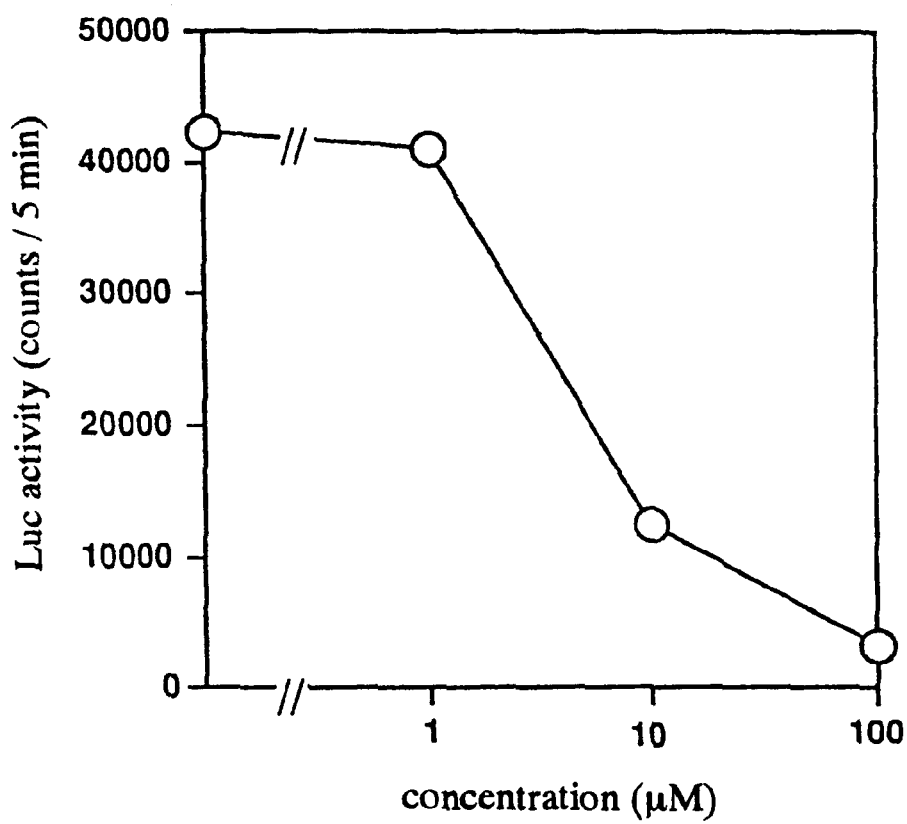
FIG. 16 shows the effects of the protease inhibitor, TLCK, on the induced gene expression by cytokines.

Proteases are considered to be involved in the activation of NF-κB through the degradation of I-κB (a protein that suppresses the activation of NF-κB in the cytoplasm; Verma, I. M. et al., (1995) Genes & Dev. 9, 2723–2735). One of the protease inhibitors, TLCK (Nacalai Tesque), is known to inhibit the iNOS induction as well as the NF-κB activation (Griscavage, J. M. et al., (1995) Biochem. Biophys. Res. Commun. 215, 721–729). The luciferase expression was measured in the same manner as in Example 5 in the presence of TLCK. It was found that TLCK suppresses the induced gene expression by IL-1 β (1 ng/ml) or CM at a concentration of about 10 μM (FIG. 16).

These experimental results also demonstrated that a system as described in Example 5 can be used to screen compounds that participate in the control of hiNOs expression.

[EXAMPLE 7]

Screening for compounds that influence the hiNOS gene expression

Figure 17:
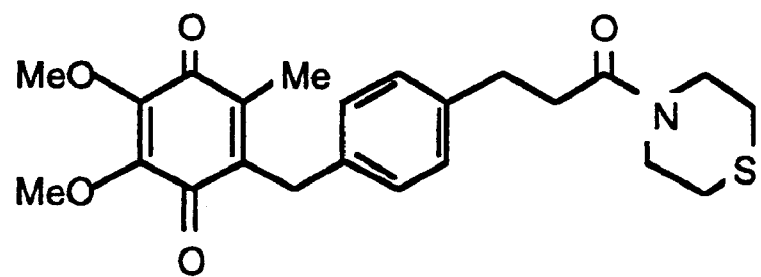
FIG. 17 shows the structural formula of Compound I, which was discovered using the screening system of the present invention.
Figure 18:
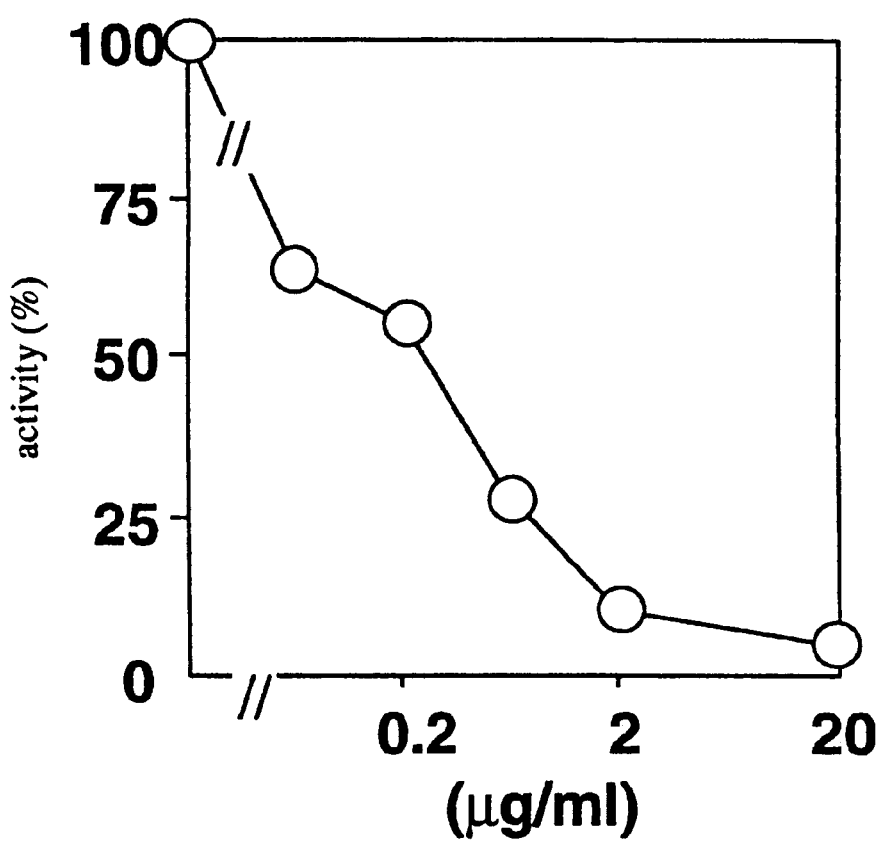
FIG. 18 shows the effects of Compound I on the screening system of the present invention.

As in Example 5, the A5 cells were spread on the 96-well plate at 10,000 cells/100 μl per well and cultured for 24 hours. Subsequently, specific compounds, which were unknown as to whether or not they influence the hiNOS gene expression, were added either individually or as mixtures and the cells were cultured for another one hour. Then, IL-1β or TNF-α was added to the culture medium to measure the luciferase activity 24 hours after the addition of IL-1 β or TNF-α in the same manner as in Example 6. As a result of screening numerous compounds and mixtures of compounds, it became clear that Compound I shown in FIG. 17 can suppresses the luciferase activity concentration-dependently (FIG. 18).

Figure 19:
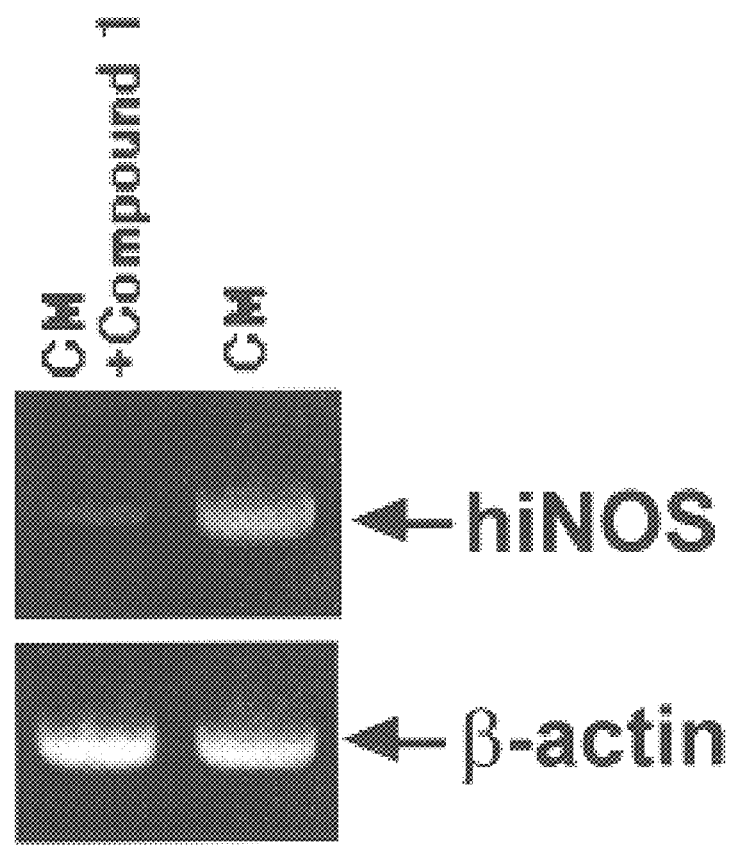
FIG. 19 is the photograph showing that Compound I suppresses the hiNOS expression at the mRNA level.

Furthermore, it was confirmed that Compound I (20 μg/ml), which was found by this screening method to suppress the hiNOS gene expression, suppresses the expression of the hiNOS mRNA in the wild-type A549 cells stimulated by CM (FIG. 19). On the other hand, Compound I at the same concentration did not influence the β-actin mRNA expression, which is constitutively expressed in the wild-type A549 cells (FIG. 19).

It is also possible to screen compounds that induce the hiNOS gene expression by a similar method to that described in Example 7, for example, by adding test compounds to A5 cells and selecting the compounds which increase the luciferase activity.

Thus, it was demonstrated that it is possible to screen compounds which influence the hiNOS gene expression by means of the screening system of the present invention.

Industrial Applicability

The present invention provides a method of simply and easily screening a compound capable of controlling the expression of human inducible nitric oxide (NO) synthase (hiNOS) with high sensitivity. The method of the present invention also enable convenient and sensitive screening of a compound that is considered to be useful for treating inflammations and sepsis by suppressing the hiNOS expression, or a compound that is considered to be useful for antitumor, antiviral, and vascular restenosis prevention treatments by inducing the expression.

We claim:

1. A DNA comprising a 3'-flanking region of the human inducible nitric oxide synthase (hiNOS) gene, wherein said 3'-flanking region confers inducible expression on an upstream coding sequence.

2. The DNA of claim 1, wherein said 3'-flanking region of the hiNOS gene has the nucleotide sequence of SEQ ID NO:16.

3. An expression controlling sequence comprising:
   (a) the DNA described in claim 1; and
   (b) a 3'-UTR of the hiNOS gene, wherein said 3'-UTR confers inducible expression on an upstream coding sequence.

4. An expression vector comprising the expression controlling sequence of claim 3.

5. The expression vector of claim 4, further comprising a reporter gene.

6. A cell transformed with the expression vector of claim 5.

7. An expression vector comprising, in order, from the 5' side:
   (a) a 5'-flanking region comprising a promoter of the hiNOS gene;
   (b) a reporter gene; and
   (c) expression controlling sequences comprising:
       (i) a 3'-flanking region of the human inducible nitric oxide synthase (hiNOS) gene; and
       (ii) a 3'-UTR of the hiNOS gene, wherein said 3'-flanking region and said 3' UTR confer inducible expression on an upstream coding sequence.

8. A method of screening a substance which induces or suppresses human inducible nitric oxide synthase (hiNOS) gene expression, comprising:
   treating a cell having an expression vector with a test substance, wherein said expression vector comprises a reporter gene, a 3'-flanking region of the hiNOS gene and a 3'-UTR of the hiNOS gene; and
   measuring a reporter gene expression level in said cell and in a control cell in the absence of said test substance, wherein a change in reporter gene expression level in said cell relative to the control indicates that the test substance induces or suppresses hiNOS gene expression.

9. The screening method of claim 8, wherein said expression vector further comprises a 5'-flanking region comprising a promoter of the hiNOS gene.

10. The screening method of claim 8, wherein said test substance is a mixture.

11. A compound which suppresses or induces hiNOS gene expression, which compound is obtained by the screening according to claim 8.

12. A pharmaceutical composition for treating diseases accompanying abnormal expression of the hiNOS gene, comprising:

a therapeutically effective amount of the compound of claim 11; and a pharmaceutically acceptable carrier.

13. A method for treating or preventing diseases accompanying abnormal expression of the hiNOS gene, comprising administering the compound of claim 11.

14. The compound of claim 11, wherein the compound 11, wherein the compound suppresses the hiNOS gene expression.

15. A pharmaceutical composition for treating diseases accompanying excessive expression of the hiNOS gene, comprising:

a therapeutically effective amount of the compound of claim 14; and a pharmaceutically acceptable carrier.

16. A method for treating or preventing diseases accompanying excessive expression of the hiNOS gene, comprising administering the compound of claim 14.

17. A kit for screening a substance which induces or suppresses hiNOS gene expression, comprising a cell transformed with an expression vector comprising a reporter gene, a 3'-flanking region of the hiNOS gene and a 3'-UTR of the hiNOS gene; and a means for measuring a reporter gene expression level.

18. A method for screening a substance which alters the activity of a specific substance that suppresses or induces hiNOS gene expression, comprising:

treating a cell comprising an expression vector with the specific substance that suppresses or induces hiNOS gene expression and a test substance, wherein said expression vector comprises a reporter gene, a 3'-flanking region of the hiNOS gene and a 3'-UTR of the hiNOS gene; and measuring a reporter gene expression level in said cell and in a control cell in the absence of said test substance, wherein a change in reporter gene expression level in said cell relative to the control indicates that the test substance alters the activity of the specific substance.

19. The screening method of claim 18, wherein said expression vector further comprises a 5'-flanking region comprising a promoter of the hiNOS gene.

20. The screening method of claim 18, wherein said test substance is a mixture.

21. A compound which alters the activity of a specific substance that suppresses or induces hiNOS gene expression, which compound is obtained by the screening method according to claim 18.

22. A pharmaceutical composition for treating diseases accompanying abnormal expression of the hiNOS gene, comprising:

a therapeutically effective amount of the compound of claim 21; and a pharmaceutically acceptable carrier.

23. A method for treating or preventing diseases accompanying abnormal expression of the hiNOS gene, comprising administering the compound of claim 21.

24. The compound of claim 21, wherein the compound suppresses the activity of the substance that induce hiNOS gene expression.

25. The compound of claim 24 having the following chemical formula:

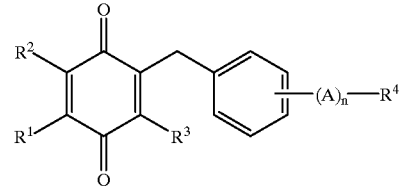

wherein $R^1$, $R^2$ and $R^3$ each independently represent a hydrogen atom, a methyl group, or a methoxy group, provided that $R^1$ and $R^2$ are not hydrogen atoms simultaneously; A represents an ethylene group or a vinylene group; n represents 0 or 1; and $R^4$ represents a hydrogen atom, a hydroxymethyl group, or a carboxyl group which may be esterified or amidated.

26. A pharmaceutical composition for treating diseases accompanying excessive expression of the hiNOS gene, comprising:

a therapeutically effective amount of the compound of claim 24; and a pharmaceutically acceptable carrier.

27. A method for treating or preventing diseases accompanying excessive expression of the hiNOS gene, comprising administering the compound of claim 24.

28. A kit for screening a substance which alters the activity of a specific substance that suppresses or induces hiNOS gene expression, comprising a cell transformed with an expression vector comprising a reporter gene, a 3'-flanking region of the hiNOS gene and a 3'-UTR of the hiNOS gene; and a means for measuring a reporter gene expression level.

\* \* \* \* \*

UNITED STATES PATENT AND TRADEMARK OFFICE
CERTIFICATE OF CORRECTION

PATENT NO. : 6,203,982 B1
DATED : March 20, 2001
INVENTOR(S) : Youichi Nunokawa et al.

It is certified that error appears in the above-identified patent and that said Letters Patent is hereby corrected as shown below:

Column 23,
Line 7, please delete "wherein the compound 11,"

Signed and Sealed this

Second Day of April, 2002

Attest:

Attesting Officer

JAMES E. ROGAN
Director of the United States Patent and Trademark Office

SEQUENCE LISTING

<160> NUMBER OF SEQ ID NOS: 17

<210> SEQ ID NO 1
<211> LENGTH: 604
<212> TYPE: DNA
<213> ORGANISM: Homo sapiens

<400> SEQUENCE: 1

```
agccagaagc gctatcacga agatatcttc ggtgctgtat ttccttacga ggcgaagaag      60
gacagggtgg cggtgcagcc cagcagcctg gagatgtcag cgctctgagg gcctacagga     120
ggggttaaag ctgccggcac agaacttaag gatggagcca gctctgcatt atctgaggtc     180
acagggcctg gggagatgga ggaaagtgat atcccccagc ctcaagtctt atttcctcaa     240
cgttgctccc catcaagccc tttacttgac ctcctaacaa gtagcaccct ggattgatcg     300
gagcctcctc tctcaaactg gggcctccct ggtcccttgg agacaaaatc ttaaatgcca     360
ggcctggcga gtgggtgaaa gatggaactt gctgctgagt gcaccacttc aagtgaccac     420
caggaggtgc tatcgcacca ctgtgtattt aactgccttg tgtacagtta tttatgcctc     480
tgtatttaaa aaactaacac ccagtctgtt ccccatggcc acttgggtct tccctgtatg     540
attccttgat ggagatattt acatgaattg cattttactt taatcacaaa aaaaaaaaaa     600
aaaa                                                                  604
```

<210> SEQ ID NO 2
<211> LENGTH: 296
<212> TYPE: DNA
<213> ORGANISM: Artificial Sequence
<220> FEATURE:
<223> OTHER INFORMATION: SV40-derived poly A addition region

<400> SEQUENCE: 2

```
ctagagtcgg ggcggccggc cgcttcgagc agacatgata agatacattg atgagtttgg      60
acaaaccaca actagaatgc agtgaaaaaa atgctttatt tgtgaaattt gtgatgctat     120
tgctttattt gtaaccatta taagctgcaa taaacaagtt aacaacaaca attgcattca     180
ttttatgttt caggttcagg gggaggtgtg ggaggttttt taaagcaagt aaaacctcta     240
caaatgtggt aaaatcgata aggatccgtc gaccgatgcc cttgagagcc ttcaac         296
```

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3

```
cttctcagcc accttggtga gg                                               22
```

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
ttctgtgcag tcccagtgag g                                          21

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
agccagaagc gctatcacg                                             19

<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6
tgtgattaaa gtaaaatgca attcatg                                    27

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
gcctggagat gtcagcgctc tg                                         22

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
ggggaacaga ctgggtgtta g                                          21

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
catttaggtg acactatag                                             19

<210> SEQ ID NO 10
<211> LENGTH: 29
<212> TYPE: DNA
<213> ORGANISM: Artificial Sequence
<220> FEATURE:
<223> OTHER INFORMATION: Primer

<400> SEQUENCE: 10
ggcgctagcc tacaggaggg gttaaagct                                  29

<210> SEQ ID NO 11
<211> LENGTH: 39
<212> TYPE: DNA

```
<213> ORGANISM: Artificial Sequence
<220> FEATURE:
<223> OTHER INFORMATION: Primer

<400> SEQUENCE: 11
gcggccgcgt cgacgattaa agtaaaatgc aattcatgt                              39

<210> SEQ ID NO 12
<211> LENGTH: 26
<212> TYPE: DNA
<213> ORGANISM: Artificial Sequence
<220> FEATURE:
<223> OTHER INFORMATION: Primer

<400> SEQUENCE: 12
gcgcggatcc ggcccactct cctaag                                           26

<210> SEQ ID NO 13
<211> LENGTH: 27
<212> TYPE: DNA
<213> ORGANISM: Artificial Sequence
<220> FEATURE:
<223> OTHER INFORMATION: Primer

<400> SEQUENCE: 13
atggcctgtc ccatggaaat ttctgtt                                          27

<210> SEQ ID NO 14
<211> LENGTH: 1026
<212> TYPE: DNA
<213> ORGANISM: Homo sapiens

<400> SEQUENCE: 14
tgagggccta caggagggt taaagctgcc ggcacagaac ttaaggatgg agccagctct        60
gcattatctg aggtcacagg gcctggggag atggaggaaa gtgatatccc ccagcctcaa      120
gtcttatttc ctcaacgttg ctccccatca agccctttac ttgacctcct aacaagtagc     180
accctggatt gatcggagcc tcctctctca aactggggcc tccctggtcc cttggagaca     240
aaatcttaaa tgccaggcct ggcgagtggg tgaaagatgg aacttgctgc tgagtgcacc     300
acttcaagtg accaccagga ggtgctatcg caccactgtg tatttaactg ccttgtgtac     360
agttatttat gcctctgtat ttaaaaaact aacacccagt ctgttcccca tggccacttg     420
ggtcttccct gtatgattcc ttgatggaga tatttacatg aattgcattt tactttaatc     480
acactgtatg cgtgtgtggg tgttttgtag ggaaagctct tctcagagtg gggagctggt     540
gggtgtcaca gcctggacag atccccgaca gagggacacc ccagccagtc catggctcct     600
ctgaaatggc tgccaggtgt gccagcagca gatggagctt cgtgctggtc caaagacctg     660
tggtagggca gggggcgcag gcctgcctcc cacacaaagt atctgaaacg gggtctggtg     720
agggtgggat tgtcgcataa ggccagtgtt tcgaggaagg ccttgagctt cttcttggac     780
actgtcttag aaagcgtttt gctctgggc caccagtctc atgcgagact gtgtgccttg     840
gccagtacgg atgtggtccc tgggaaggca gcgtgtcgag gcgagtgtgg gccacaacat     900
cctcgcctga gggactgggg accctcttgg gtttggagca ggccaaggaa tccttcttag     960
gagagtgggc cccgtttcct tctcctggtc agaacccaaa aggagctca gcggcggcca    1020 ctgggg                                                              1026

<210> SEQ ID NO 15
<211> LENGTH: 35
```

```
<212> TYPE: DNA
<213> ORGANISM: Homo sapiens

<400> SEQUENCE: 15
aactgtacac aagctgggga cactcccttt ggaaa                             35

<210> SEQ ID NO 16
<211> LENGTH: 544
<212> TYPE: DNA
<213> ORGANISM: Homo sapiens

<400> SEQUENCE: 16
actgtatgcg tgtgtgggtg ttttgtaggg aaagctcttc tcagagtggg gagctggtgg    60
gtgtcacagc ctggacagat ccccgacaga gggacacccc agccagtcca tggctcctct   120
gaaatggctg ccaggtgtgc cagcagcaga tggagcttcg tgctggtcca aagacctgtg   180
gtagggcagg gggcgcaggc ctgcctccca cacaaagtat ctgaaacggg gtctggtgag   240
ggtgggattg tcgcataagg ccagtgtttc gaggaaggcc ttgagcttct tcttggacac   300
tgtcttagaa agcgttttgc tctggggcca ccagtctcat gcgagactgt gtgccttggc   360
cagtacggat gtggtccctg ggaaggcagc gtgtcgaggc gagtgtgggc cacaacatcc   420
tcgcctgagg gactggggac cctcttgggt ttggagcagg ccaaggaatc cttcttagga   480
gagtgggccc cgtttccttc tcctggtcag aacccaaaaa ggagctcagc ggcggccact   540
gggg                                                               544

<210> SEQ ID NO 17
<211> LENGTH: 26
<212> TYPE: DNA
<213> ORGANISM: Homo sapiens

<400> SEQUENCE: 17
atggcctgtc cttggaaatt tctgtt                                       26
```